United States Patent
Delk et al.

[11] Patent Number: 5,300,037
[45] Date of Patent: Apr. 5, 1994

[54] MEDICAL CONDUIT HOLDER

[75] Inventors: Robert E. Delk, Dallas; Michael L. Bowen, Arlington; Sharon D. Cheatwood, Dallas, all of Tex.

[73] Assignee: Ansley Medical Products, Inc., Dallas, Tex.

[21] Appl. No.: 3,735

[22] Filed: Jan. 13, 1993

[51] Int. Cl.$^5$ ............................................. A61M 5/32
[52] U.S. Cl. ........................ 604/180; 128/DIG. 26; 24/306
[58] Field of Search ........................ 604/180, 179, 174; 128/DIG. 15, DIG. 26; 24/306, 442; D24/127, 128

[56] References Cited

U.S. PATENT DOCUMENTS

| | | |
|---|---|---|
| 3,288,136 | 11/1966 | Lund . |
| 3,677,250 | 7/1972 | Thomas . |
| 3,726,280 | 4/1973 | Lacount . |
| 3,765,421 | 10/1973 | Poprick . |
| 3,834,380 | 9/1974 | Boyd .................... 604/180 |
| 3,878,849 | 4/1975 | Muller et al. . |
| 3,977,393 | 8/1976 | Kovacic ............ 128/DIG. 15 |
| 4,074,397 | 2/1978 | Rosin .................... 24/306 |
| 4,165,784 | 8/1979 | Johnson . |
| 4,308,642 | 1/1982 | Heyman ................ 24/306 |
| 4,333,468 | 6/1982 | Geist ..................... 604/179 |
| 4,484,914 | 11/1984 | Brown .................. 604/180 |
| 4,571,245 | 2/1986 | Hubbard et al. ........ 604/179 |
| 4,583,976 | 4/1986 | Ferguson ............... 604/174 |
| 4,617,017 | 10/1986 | Hubbard et al. ........ 604/179 |
| 4,702,736 | 10/1987 | Kalt et al. .............. 604/180 |
| 4,726,716 | 2/1988 | McGuire ................ 604/180 |
| 5,073,170 | 12/1991 | Schneider ............. 604/180 |
| 5,100,393 | 3/1992 | Johnson ................ 604/110 |
| 5,147,322 | 9/1992 | Bowen et al. ........... 604/180 |

FOREIGN PATENT DOCUMENTS

| | | | |
|---|---|---|---|
| 2233902 | 1/1991 | United Kingdom ............. 604/180 |
| 2235629 | 3/1991 | United Kingdom ............. 604/180 |
| 9112045 | 8/1991 | World Int. Prop. O. ......... 604/110 |

OTHER PUBLICATIONS

Utah Medical Brochure, Page Showing Tube Holder of APLIX, Inc. circa 1990.

Primary Examiner—John G. Weiss

[57] ABSTRACT

A unitary medical conduit holder for securing medical conduits to the skin of a patient is made of two major portions which are sonically welded or otherwise attached to one another. The first portion is a base plate or patch for adhesively securing to the skin. The second portion is a strap with wide and narrow ends which fold in opposite directions fully encircle the conduit or a bundle of conduits. Complementary pressure sensitive VELCRO type attachment surfaces are present on the upper surfaces of the base plate and the strap. In the final use position the externally exposed parts of both the base patch and the strap are smooth so as not to snag on surrounding materials. The surface of the strap which contacts the bottom of the conduit is made of or coated with a high friction material to prevent axial slipping of the encircled conduit. Typical conduits which may be conveniently held in place with this invention include tubes, lumens, catheters, electrical wiring, and optical fibers. The conduits may easily be removed or replaced without the necessity of removing the adhesive from the patient.

13 Claims, 3 Drawing Sheets

MEDICAL CONDUIT HOLDER

BACKGROUND OF THE INVENTION

1. Field of the Invention

The present invention relates generally to a temporary clamp or holder for adjustably securing a conduit adjacent the surface of an object and more particularly to a clamp capable of holding medical conduits to a patient's body in conjunction with numerous medical treatments and procedures. It will be understood the term conduit is used in the broadest sense in this disclosure and might equally apply to a tube for transporting a fluid, a wire or other medium for transporting electromagnetic energy, or simply a rod for transporting thermal energy. Thus, in the broad sense, this invention is useful for firmly holding any long slender conduit of indefinite length, such as a tube, pipe, optical fiber, or electrical wire, adjacent and parallel to an attachment or mounting surface. Generally the mounting surface is the epidermal layer of a human patient since it is so often crucial to provide conduit support near a point of entry of a conduit into the interior of the body. However, upon occasion, it may prove useful to support a medical conduit from a nearby physical object such as a bedrail, etc. The medical conduit holder of this invention proves ideal for use with a large variety of mounting surfaces. There is no requirement that the mounting surface be planar or regular in any way. Many medical treatments and procedures require the transient use of external and mesentery conduits and thereby require apparatus for temporarily holding the conduits in place in a convenient and inexpensive manner. As a result the invention applies to numerous and diverse specialties within the medical field. For example, lumen injection cannulae, feeding tubes, nasogastric tubes, Foley catheter and condom catheter tubes, dialysis tubes, angiocath and heparin lock set tubes, luer locks as well as other tubes used to introduce liquids into the body intravenously or to introduce oxygen into the mouth or nose of the patient may be adequately supported by means of this invention. Electrical wiring and other patient monitoring type conduits may also be conveniently held in place so as to prevent entanglement or dislodging during patient movement.

2. Description of the Prior Art

There has long been a need for a simple but universal tube, lumen, and conduit (TLC) holder for bedridden patients. For years adhesive tape attached directly to the skin and wrapped about the tube was the best device available for releasably but firmly retaining conduits upon a patient. Rarely do medical personnel have the skill to make a proper mesentery support using ordinary hospital self adhesive tape for holding a catheter or tube to the skin. Tape has proven unsatisfactory because it must be removed from the patient each time the conduit must be moved or changed, causing discomfort to the patient and skin irritation. Conduits of this nature often need to be reoriented or replaced requiring frequent irritating pulling of adhesive tape support structure from the sensitive epidermal layer of the patient. Various devices for holding either an injection cannula, catheter tubing or an infusion tube in place have been developed heretofore. Many prior conduit holders have made it difficult or impossible to adjust or replace the conduits without completely removing the conduit holder from its mounting surface. Prior conduit holders have also been difficult or impossible to trim to size for fitting to the patient. Many prior holders suffer from an inability to firmly hold long slender conduits in their lengthwise direction. In other words it was easy for the captured conduit to slide longitudinally with respect to the holder. This longitudinal sliding can be either desirable or undesirable, depending on the situation, and should therefore be under the control of the user as is accomplished with this invention. Another common problem with prior conduit holders is that they tend to get caught in bed linen and clothing due either to excess bulkiness or exposed tacky surfaces.

U.S. Pat. No. 3,288,136 issued to Lund on Nov. 29, 1966 shows a tube lock for releasably anchoring a medical tube to the skin of a patient. Lund uses VELCRO fastening means and an auxiliary tube to secure the tubing against lengthwise movement. The auxiliary tube causes the Lund device to be useful only for tubing of a certain diameter. In contradistinction, the instant invention may securely hold tubes or bundles of tubes of any diameter.

U.S. Pat. No. 3,677,250 issued to Thomas on Jul. 18, 1972 shows a tabbed anchoring tape means for anchoring medical tubing. Thomas's tape is adhered to the skin of the patient and wrapped around the tubing but uses no easily releasable reusable attachment means and in no other way resembles the instant invention.

U.S. Pat. No. 3,834,380 issued to Boyd on Sep. 10, 1974 shows a holder for intravenous injection cannula and tubing. Body uses a separate clamping tube in the form of a slit hollow cylinder for supporting the catheter tube which is in turn held shut by a VELCRO strip. This holder is not adaptable to different sized or multiple tubing. In contradistinction, the instant invention will hold conduits of all sizes, and multiple conduits.

U.S. Pat. No. 3,878,849 issued to Muller et al on Apr. 22, 1975, U.S. Pat. No. 3,765,421 issued to Poprick on Oct. 16, 1973, and U.S. Pat. No. 3,726,280 issued to Lacount on Apr. 10, 1973 show catheter or surgical tube supports which are designed to encircle a limb of the patient. In contradistinction, the instant invention does not require the encircling of a limb to establish a firm support base.

U.S. Pat. No. 4,165,784 issued to Johnson on Aug. 28, 1979 shows a catheter tube holder forming a double bridge member that loosely encircles the tube. The Johnson holder does not prevent longitudinal slippage of the tube and is therefore limited in application. In direct contradistinction thereto, the instant invention may be infinitely adjusted to grip firmly various sizes and quantities of tubes, while preventing longitudinal slippage of the tubes; accordingly, the instant invention provides a virtually unlimited range of applications.

U.S. Pat. No. 4,333,468 issued to Geist on Jun. 8, 1982 shows a mesentery tube holder apparatus for adhesive attachment of a tube to a patient's body. Geist's support does not completely encircle the tubing or provide uniform clamping pressure about the circumference thereof. Geist's holder is not adaptable to a wide range of different tubing diameters nor is it suitable for simultaneously holding several pieces of tubing. In contradistinction, the instant invention completely encircles the medical conduit with a bidirectional wrapping, allows a significantly greater total holding force without tube deformation, and is suitable for multiple or variable diameter tubing.

U.S. Pat. No. 4,583,976 issued to Ferguson on Apr. 22, 1986 shows a catheter support adhesively attached to the skin. The support does not completely encircle the tubing or provide uniform clamping pressure about the circumference thereof. Ferguson's holder is not adaptable to a wide range of different tubing diameters nor is it suitable for simultaneously holding several pieces of tubing. By way of contradistinction, the instant invention completely encircles the medical conduit with a bidirectional wrapping, allows a significantly greater total holding force without tube deformation, and is suitable for multiple or variable diameter tubing.

U.S. Pat. No. 4,571,245 issued to Hubbard et al on Feb. 18, 1986 shows a personal catheter leg strap which appears, at least superficially, like the instant invention in that they both employ VELCRO fastened straps encircling a catheter tube. However, in direct contradistinction the instant invention, Hubbard's holder must be wrapped around a limb of the patient thus limiting its use to the area of the limbs. Hubbard's holder can only be oriented in a fixed direction with respect to the limb it encircles. Hubbard's conduit strap must be wrapped an additional half turn about the tubing so as to prevent the artificial burr material from exterior exposure. However, this direction of wrapping makes the support weaker by requiring the VELCRO attachment points to be located some distance from the supported tube. Hubbard does not address the problem of axial slippage of the supported tube in this patent.

U.S. Pat. No. 4,617,017 issued to Hubbard et al on Oct. 14, 1986 is a continuation-in-part of the above mentioned U.S. Pat. No. 4,571,245. This patent specifically addresses the axial slippage problem but otherwise suffers from the same disadvantages mentioned above.

U.S. Pat. No. 4,702,736 issued to Kalt et al on Oct. 27, 1987 shows a tubing clamp utilizing a conduit strap having VELCRO fastening means for adhering a medical tubing between a resilient pad on the strap and a resilient base. Kalt's holder does not completely encircle the tubing or provide uniform clamping pressure about the circumference thereof. Kalt's holder is not adaptable to a wide range of different tubing diameters nor is it suitable for simultaneously holding several pieces of tubing. By way of contradistinction, the instant invention completely encircles the medical conduit with a bidirectional wrapping, allows a significantly greater total holding force without tube deformation, and is suitable for multiple or variable diameter tubing.

U.S. Pat. No. 4,726,716 issued to McGuire on Feb. 23, 1988 shows a fastener exclusively made to hold Foley catheters. Since the device has an opening for inserting a second passage of the catheter, McGuire's catheter holder will only work with Foley type catheters. In contradistinction, the instant invention enfolds the tubing from two directions with straps firmly attached to a large area adhesive base plate.

U.S. Pat. No. 5,147,322 issued to Bowen et al on Sep. 15, 1992, in which a named coinventor therein, Michael L. Bowen, is the same person named as a coinventor in the instant application, teaches a catheter tube holder including a double base member with an integral tube holder extended upwardly from the center of the base. The holder includes a slot through which the tab end of the holder is inserted, after the tab main body is wrapped around a catheter tube, and the tab end is provided with hook type fasteners cooperating with the loops of a loop strip on the top surface of one side of the double base member. Wrapping the tube is a two handed operation and one must carefully insert the "hook" tab end through a very small aperture to avoid the hook catching on the loop portion of the base. In contradistinction, the bidirectional enfolding of the two straps of the instant invention can be accomplished quickly and easily with one hand, since the straps are simply folded over the tube. There is no "threading" involved due to the provision of a cutout of substantial dimensions in the large strap.

The brochure of Utah Medical of Midvale, Utah shows a tube holder of APLIX Inc. which is of unknown date (circa 1990) but is believed to qualify as prior art with respect to this invention. The APLIX holder makes no provision for securement against lengthwise movement of the tubing and exposes VELCRO hooks to the surroundings. By contrast, the instant invention has at least a limited range of directional adjustment, provides bidirectional endfolding for stopping lengthwise movement, and does not expose VELCRO hooks to the surroundings.

None of the above inventions and patents, taken either singly or in combination, is seen to describe the instant invention as claimed.

SUMMARY OF THE INVENTION

This invention provides a belt like, wraparound, adhesive medical conduit holder. A bidirectional strap portion is sonically welded or otherwise permanently attached to a relatively large base portion to form the holder. The single piece unit thus formed is simpler to use, ship, and distribute than would be a multiple piece unit. The base portion is adhesively attached to the skin of the patient or another convenient support surface at the time of use. A medical grade adhesive compatible for use on a living body is used. Separate ends of the strap extend in opposite directions normal to the medical conduit. Subsequent to placing the conduit atop the strap the ends are folded in opposite directions over the conduit and attached by pressing to the upper surface of the base portion, preferably by means of a hook and loop type fastener such as VELCRO. In this manner the medical conduit is very firmly, but yet releasably, held adjacent and parallel to the support surface. A low profile assures the rigidity of the attachment in the lateral direction of the conduit and the multiple oppositely folded straps can selectively assure a firm grip in the longitudinal direction of the conduit. Limited reorientation or conduit exchanges may be made without removal of the adhesive from the patient. The large base portion may easily be trimmed to size for special purposes such as for use on infants. The straps are folded in two directions so as to hold the conduit next to the skin with a minimal amount of play and, at the same time, provide a selective degree of resistance to longitudinal sliding of the conduit. The "hooks" of the VELCRO are on the originally outward side of the strap portion whereas the "loops" are on the side of the base portion opposite the adhesive. The portion of the strap near the sonic weld region and adjacent the conduit in the wrapped condition may optionally be coated with a high friction material to further resist axial slippage. The surface of the straps facing outward from the conduit in the wrapped condition have a smooth exterior so as not to accidentally grab upon foreign material.

Accordingly, it is a principal object of the invention to provide a medical conduit holder for holding a conduit on the body of a patient which may be packaged and distributed as a single piece item suitable for use in a hospital environment.

Accordingly, it is another object of the invention to provide a medical conduit holder for holding a conduit on the body of a patient which is directionally adjustable so as to vary the orientation of the conduit with respect to the patient.

It is another object of the invention to provide a medical conduit holder wherein the conduit may be removed or reoriented without tearing any adhesive bonds from the skin of the patient.

It is a further object of the invention to provide a medical conduit holder which presents no external protuberances, corners, or edges to catch upon or otherwise bind with surrounding objects such as bed linens, other bandages, or clothing.

Still another object of the invention is to provide a medical conduit holder which is fully operational to hold one or a bundle of several conduits of virtually any type, firmness, shape, or size.

Still another object of the invention is to provide a medical conduit holder suitable for holding conduits fully capable of transmitting bodily fluids, electrical signals, or light waves.

Still another object of the invention is to provide a medical conduit holder which provides a positive non-flopping support for the conduit by securing the conduit to the patient's skin surface very near the portion of the conduit which is closest the skin surface.

Still another object of the invention is to provide a medical conduit holder which fully enfolds the held conduit with dual straps so as to provide maximum holding power when the straps are tightly countertensioned against one another and limited longitudinal sliding when the straps are more loosely countertensioned.

Still another object of the invention is to provide a medical conduit holder which may include a high friction coating on the lower portion adjacent the conduit so as to provide maximum gripping power and in particular to prevent slippage of the conduit in its longitudinal direction.

Still another object of the invention is to provide a medical conduit holder which distributes the total holding force over a relatively large area of the conduit to thus provide a large holding force with a relatively low pressure and consequent minimal constriction of the held conduit.

Still another object of the invention is to provide a medical conduit holder which is easily releasible from the conduit so that the tubing may be replaced without replacing or disturbing the original orientation of the holder.

Still another object of the invention is to provide a medical conduit holder which may be trimmed to conveniently fit upon virtually any area of a patient's skin surface be they infant or adult.

Still another object of the invention is to provide a medical conduit holder which is formed as a unitary piece from a separate adhesive base portion and a multiple strap portion.

Finally, it is a general object of the invention to provide improved elements and arrangements thereof in an apparatus for the purposes described which is inexpensive, dependable and fully effective in accomplishing its intended purposes.

It is submitted that the present invention meets or exceeds all the above objects and goals. Upon further study of the specification, drawings, and appended claims these and other objects and advantages of the present invention will become readily apparent.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

Similar reference characters denote corresponding features consistently throughout the attached drawings.

DETAILED DESCRIPTION OF THE PREFERRED EMBODIMENT

Figure 1:
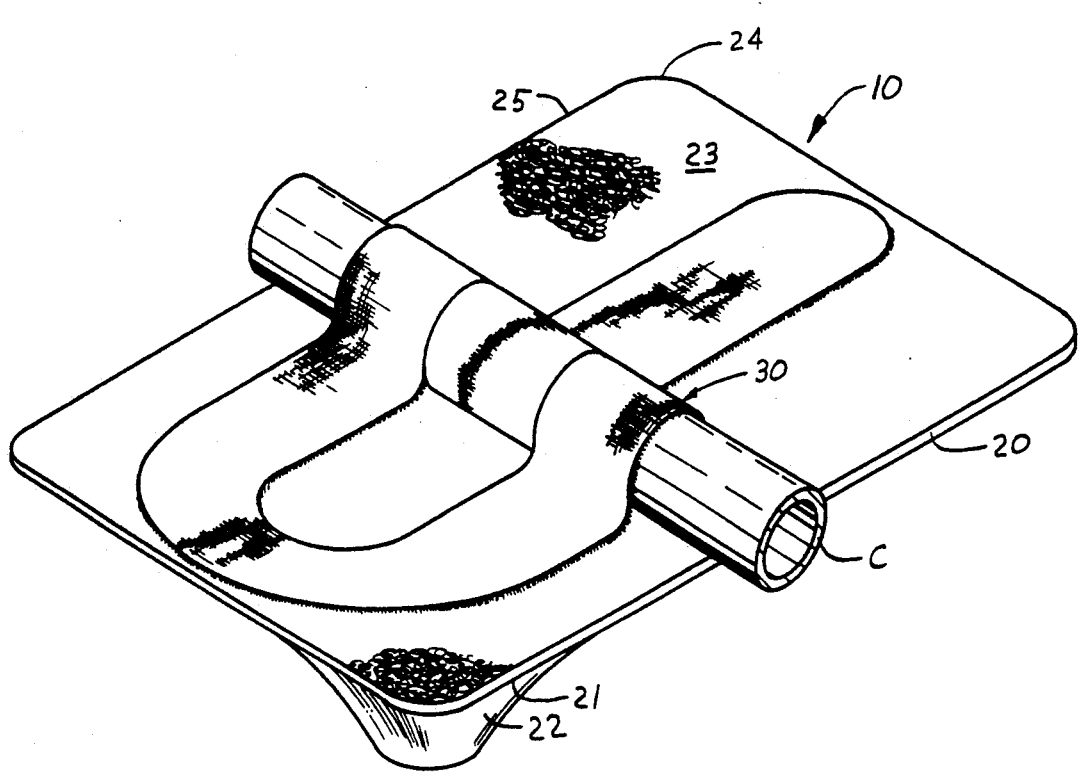
FIG. 1 is a perspective view of the medical conduit holder shown in an operative position holding a cut away piece of medical tubing.

Referring now to FIG. 1, medical conduit holder 10 is shown holding a typical portion of medical conduit C. It should be understood from the outset that medical conduit C, shown as a piece of tubing cut off to a short length for clarity of illustration only, could represent fluid tubing, electronic wiring, fiber optic strands, or any other elongated object used in conjunction with modern medical procedures. The material from which holder 10 is constructed is mechanically strong, light and pliable, electrically insulative and non-inductive, magnetically permeable, thermally non-conductive, and chemically inert. It is contemplated that an entire bundle comprising many different sizes and types of medical conduits could be enfolded as a unit and supported by the holder of this invention. The phrase "medical conduit" is meant to include tubing of all sizes and types both rigid and flexible for transporting fluids to and from the body, electrical wiring for transmitting electrical signals to or monitoring signals from the body, and optic fibers for similar transmission of light signals.

The TLC holder 10 comprises base plate 20 and strap portion 30. Base plate 20 is formed of a moderately pliable material that will contour to a patient's skin and still be easy to trim to size for special applications such as for use with infants. The lower portion of the base plate 20 is covered with a medical grade self adhesive coating 21 compatible for use on a living body. Substrate film 22 covers the adhesive 21 for shipping and handling and is designed to be peeled away and discarded at the use site in the conventional manner. A hypoallergenic synthetic acrylic pressure sensitive adhesive may be used. More specifically, a homogeneous blend of one or more water soluble and/or water swellable hydrocolloids dispersed in a viscous elastomeric substance such as polyisobutylene may be used as is well known in the adhesive art. Alternately, the adhesive composition can also include one or more cohesive strengthening agents or one or more hydratable natural or synthetic polymers. Since it is contemplated the base plate may be left upon the patient for relatively long periods of time (through several changes of conduits C) it is particularly important that the adhesive chosen be non irritating to the skin. Preferably, it should also be semi-porous or air permeable so as not to completely seal the covered skin area from at least limited contact with the atmosphere. A suitable adhesive for this purpose is manufactured by Minnesota Mining and Manufacturing Corporation (3M) and is sold as part #9879.

Base plate 10 is shown as being substantially rectangular with rounded corners. This configuration is preferable as a starting shape for the base because it allows for easy packaging, attachment and trimming. This invention is adaptable to limited adjustment of the mounting angle of the medical conduit with respect to the base plate. The placement of the conduit C upon base plate 20 is more fully described hereinafter. Corners of the square base plate are rounded as shown at 24 to reduce stress concentrations and thus prevent inadvertent peeling of the base from the patient. It is to be understood that the base plate may be easily trimmed to fit as needed for application to any special area of the skin such as the facial area. It will also be understood that the overall size of the base plate 20 and its unitary strap portion 30 may be varied over a wide range with the only requirement being that the base plate be large enough to accommodate the strap portion. To facilitate the desired air permeability base plate 20 may be perforated with a multitude of micro pores or small holes if desired.

The upper surface 23 of base plate 20 is covered with loop type VELCRO material so as to present a smooth exposed surface while serving as a convenient and large attaching point for the hook type VELCRO material of strap portion 30. For convenience of illustration only patches of the loop type material are shown but, be it understood, the entire upper surface of base plate 20 could conveniently be covered with such material. Since strap portion 20 is fixed to the base portion 20 it is recognized that only the portion of the base that is actually contacted by the folded straps need be covered with the hook type VELCRO material. Economies of manufacture could result from this arrangement and it should be recognized that the scope of this invention is intended to cover such variations.

Figure 2:
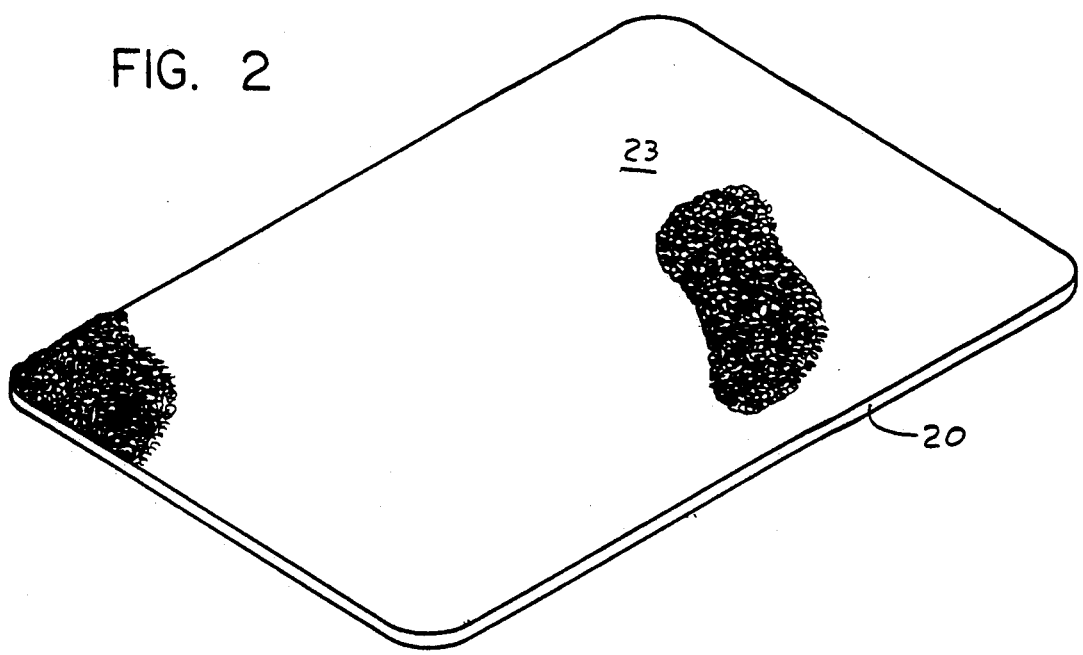
FIG. 2 is a perspective view of the base portion of the medical conduit holder prior to attachment of the strap portion.
Figure 3:
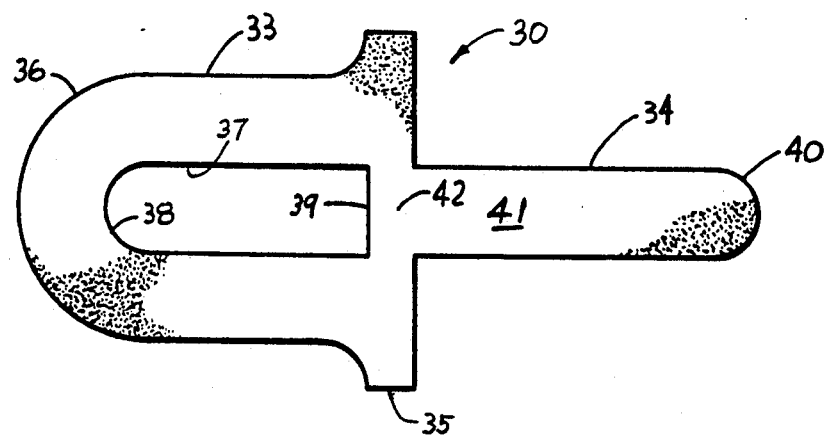
FIG. 3 is top plan view of the strap portion of the medical conduit holder prior to attachment of the base portion.
Figure 4:
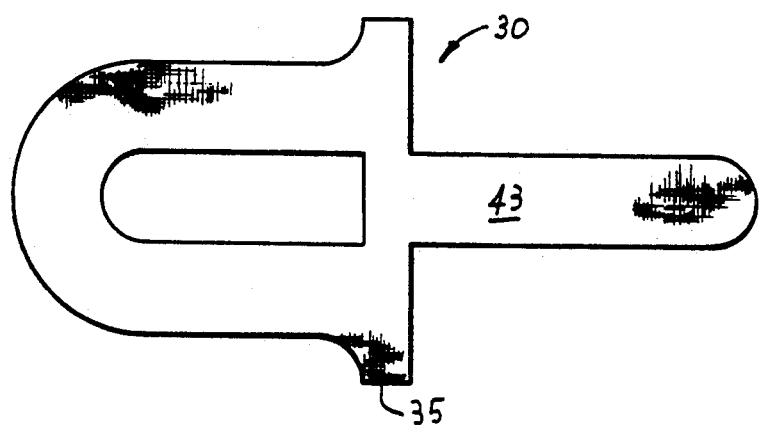
FIG. 4 is bottom plan view of the strap portion of the medical conduit holder prior to attachment of the base portion.
Figure 5:
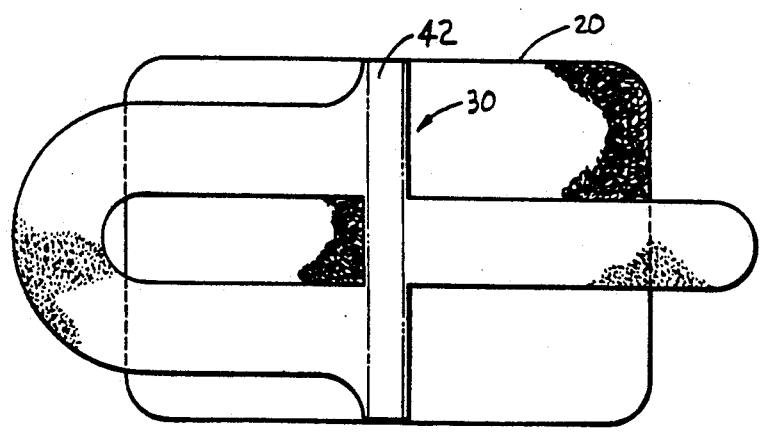
FIG. 5 is a top plan view of the unitary medical conduit holder after joining of the base and strap portions and as it appears when unwrapped and laid flat before use.

FIG. 2 shows the separate base portion 20 as it would appear prior to manufacture of the unitary medical conduit holder by attaching the strap portion 30 as shown in FIGS. 3 and 4 from top and bottom. FIGS. 3 and 4 show separate strap portion 30 unwound and laid flat as it would appear prior to attachment to base portion 20 as shown in FIG. 5. Strap 30 is generally a rectangular strip being wider at left end 33 than the right end 34 and wider still in a relatively short central zone 35 as seen in FIGS. 3 and 4. An elongate central cutout 37 is formed in left end 33 strap bounded with semicircular edge 38 on the left and straight edge 39 near the central zone 35 between wide 33 and narrow 34 portions of the strap. The wide end is rounded as at 36 so as to be parallel with semicircular edge 38 of cutout 37 and the narrow end is rounded at the far right as at 40. The top surface 41 of strap 30 is made from hook type VELCRO material complementary with and attachable by gentle pressure to the loop type material 23 on the top of base portion 20. The central portion 42 (FIG. 5) of top surface 41 of strap portion 30 need not be covered with artificial briar material for satisfactory operation of the invention. As discussed above in regard to the loop type material on base portion 20 the hook type material need only be formed where it is needed to form the ultimate attachment of the straps to the base in use. The bottom surface of strap portion 30 is a generally smooth backing material. As an alternative, central zone 35 of the upper surface 41 of strap portion 30 may be coated with a high coefficient of friction material to discourage longitudinal sliding of the enfolded medical conduit. A high friction or tacky type material layer may be bonded or otherwise attached to the main strap portion for this purpose. It is contemplated that the bonding of this adhesive material may be combined with the step of attaching the strap portion 30 to the base portion 20 to be described later.

FIG. 5 shows the strap portion 30 placed atop base portion 20 in the position in which the two portions will be sonically welded or otherwise permanently attached to one another. It is contemplated that a thermosetting glue may also be used for this attachment. In general it is merely required to place strap portion 30 centrally atop base portion 20 and apply heat or sonic energy to the narrow central area 42 outlined in phantom in FIG. 5.

Figure 6:
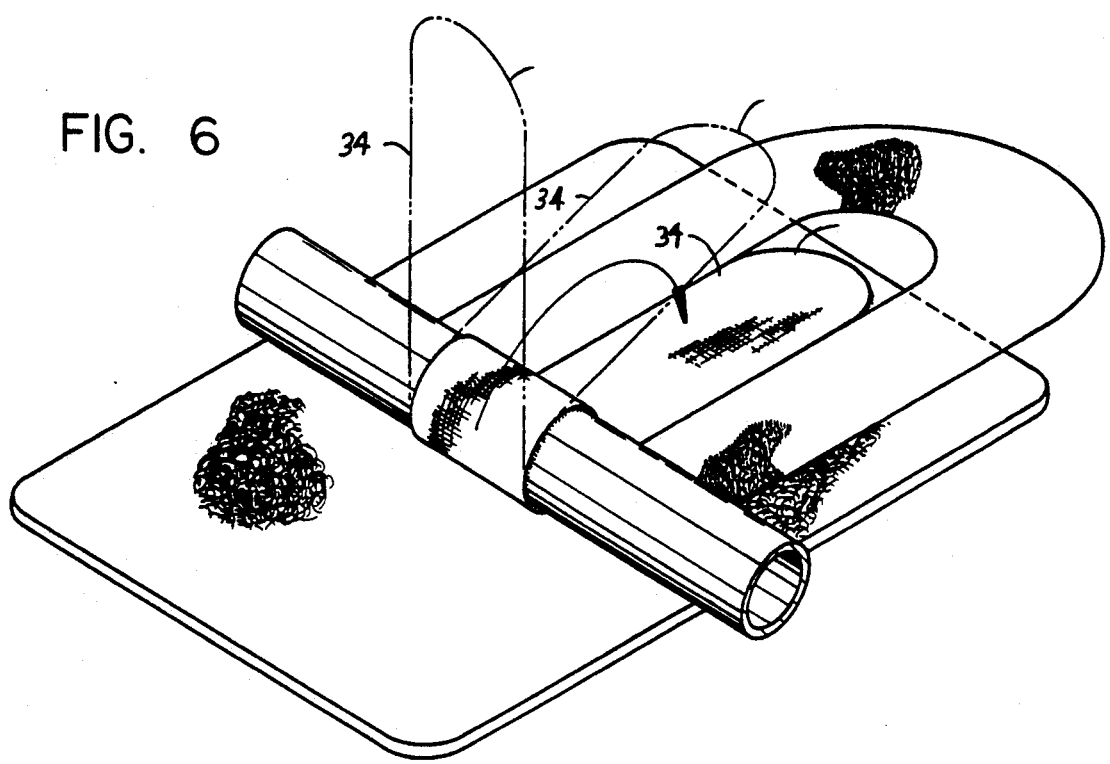
FIG. 6 is a perspective view of the medical conduit holder shown in FIG. 5 illustrating the first step of a strap folding process in phantom lines.
Figure 7:
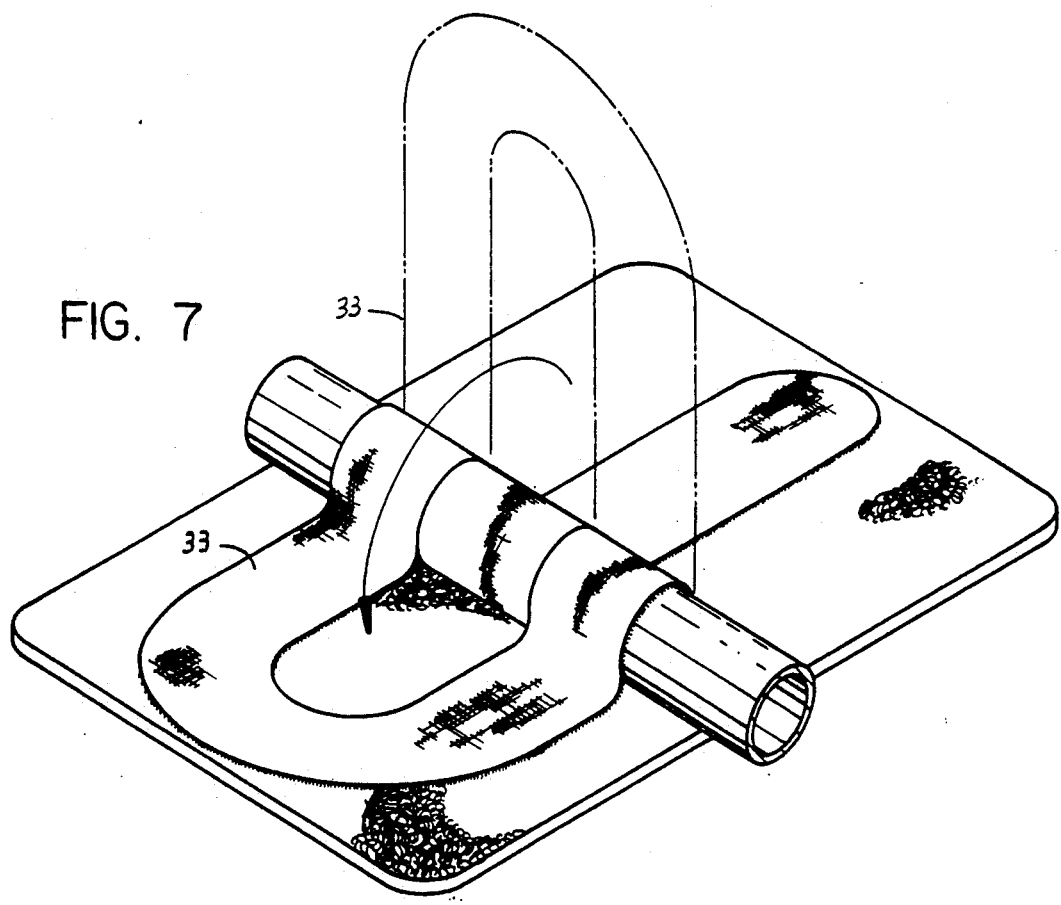
FIG. 7 is a perspective view of the medical conduit holder shown in FIG. 6 illustrating the final step of a strap folding process in phantom lines.

The reasons for arranging the various surfaces and parts as just described will become more apparent from the following description of the use of the invention and with reference to FIGS. 6 and 7.

To use the medical conduit holder described, the following procedure will generally be used. First the adhesive side 21 of the base plate portion of the holder will be exposed by peeling away the substrate covering 22. Then the base plate is placed upon or near the patient at the desired area of medical conduit support.

Next, the medical conduit or conduits to be secured are placed atop the strap portion of the holder. The conduit is placed upon the area of the strap portion which may have been coated with tacky material as discussed above. The narrow strap 34 is folded up and over the tubing and attached with the VELCRO by pressing against base surface 23 which is exposed through cutout 37. This clockwise folding is shown in various stages in phantom lines in FIG. 6. The conduit is now firmly positioned atop the high friction portion of the strap at approximately a 90 degree angle to the long dimension of the strap.

Next, the wide end of strap is folded over the conduit in the opposite direction, tensioned against the conduit, and pressed back down against the VELCRO on base 20. The counterclockwise direction of the second fold is clearly shown in FIG. 7. Alternately, at this point, pulling on the opposite ends 33 and 34 of the strap prior to pressing them to the VELCRO will tightly constrict and firmly secure the medical conduit in such a manner as to prevent any unwanted motion. If, as may be desired, the conduit is to be allowed a degree of longitudinal freedom, the narrow and wide strap portions 34, 33 may be pressed to the base 20 without tensioning thus restraining the conduit from radial movement while allowing the conduit to slide lengthwise through the confining loop.

Note that when the conduit has been enfolded in this manner the most exposed surfaces are all smooth. The conduit holder of this invention presents this smooth surface to the environment so as to eliminate unwanted snagging on other objects in the environment and accomplish one of the major goals of the invention. Also note that when the strap is folded in this manner, the high friction or tacky central section of the strap 42 as seen in FIG. 5 is smoothly and tightly pressed against the conduit thus eliminating unwanted lengthwise slipping of the conduit and accomplishing another of the major goals of the invention. Additionally note that when the strap is folded in this manner, the tensioning of the wide and narrow portions of the strap against one another causes both to press downwardly on the conduit toward the patient's skin thus providing a connection with no play and accomplishing another major goal of the invention.

An additional feature and object of the invention is achieved by preconnecting the strap and base portions prior to use. These variations are taught here in the expectation that the scope of patent protection, limited only by the appended claims, will include such variations.

It is to be understood that the provided illustrative examples are by no means exhaustive of the many possible uses for my invention. From the foregoing description, one skilled in the art can easily ascertain the essential characteristics of this invention and, without departing from the spirit and scope thereof, can make various changes and modifications of the invention to adapt it to various usages and conditions.

It is to be understood that the present invention is not limited to the sole embodiment described above, but encompasses any and all embodiments within the scope of the following claims.

We claim:

1. A conduit holder for releasably securing medical conduit to the external skin surface of a patient comprising:
    base plate means having a substantial area and comprising;
        a pliable support substrate easily contourable to a skin surface,
        a generally smooth upper attachment area, and
        a lower surface coated with medical grade adhesive for semi-permanent attachment to the skin of the patient, and
    strap means having a substantial length for folding over said conduit and adjustably but firmly securing said conduit generally parallel to the skin surface and orthogonal to said strap length, said strap means having wide and narrow ends and a central transition zone between said ends, there further being a cutout centrally located in said wide end, said cutout having a width just sufficient to allow unimpeded passage of said narrow end through said cutout and at the same time urging said narrow end to remain axially aligned with said wide end after folding over said conduit;
    said strap means being firmly secured to said base plate means along said central transition zone; and
    pressure sensitive attachment means for holding said strap means to said upper attachment area on opposite sides of said conduit.

2. The conduit holder according to claim 1 wherein said strap means central transition zone is generally smooth; and
    said strap means further comprises;
        a generally smooth lower surface; and
        a generally rough upper surface which, together with said generally smooth upper attachment area of said base plate means, forms said pressure sensitive attachment means;
        said cutout centrally located in said wide end extending from near its outer end to near said central transition zone.

3. The conduit holder according to claim 2, wherein said wide and narrow ends of said strap means are folded in opposite directions over said conduit from under said conduit, up around said conduit, and back down on opposite sides of said conduit.

4. The conduit holder according to claim 2, wherein said generally rough upper surface of said strap means includes a central band of high friction material for tightly gripping said conduit after folding opposite ends of said strap means over said conduit, said high friction band extending fully across the width of said strap and in approximately the region of said central transition zone.

5. The conduit holder according to claim 2, wherein said generally rough upper surface of said strap means is turned inward upon said base plate after folding over said conduit so as to present a smooth opposite external surface to the surrounding environment.

6. The conduit holder according to claim 4, wherein said generally rough upper surface of said strap means is interrupted by a relatively tacky central band for presenting a high friction surface to said conduit and providing longitudinal stability.

7. The conduit holder according to claim 1, wherein said base plate means further comprises a sheet for covering said adhesive coating which is easily removed when it is desired to attach said base plate means to the skin of the patient.

8. The conduit holder according to claim 1, wherein said base plate means may be easily trimmed to fit awkward areas of the patient without compromising its effectiveness in providing secure attachment means for said medical conduit.

9. A conduit holder for releasably securing medical conduit to the external skin surface of a patient comprising;
    base plate means comprising;
        a pliable support surface easily contourable to a skin surface,
        a generally smooth upper attachment area, and
        a lower surface coated with medical grade adhesive for semi-permanent attachment to the skin of the patient, and
    strap means having a substantial length for folding over said conduit and adjustably but firmly securing said conduit generally parallel to the skin surface and orthogonal to said strap length, said strap means having wide and narrow ends and a generally smooth central transition zone between said ends and comprising;
        a generally rough upper surface including a central band of high friction material for tightly gripping said conduit after folding said strap means around said conduit, said high friction band extending fully across the width of said strap in the region of said central transition zone between said wide and said narrow end of said strap means;

said generally rough upper surface, together with said generally smooth upper attachment area of said base plate means, forms pressure sensitive attachment means for holding said strap means to said upper attachment area on opposite sides of said conduit and a cutout centrally located in said wide end near said transition zone, said cutout having a width just sufficient to allow unimpeded passage of said narrow end through said cut out and at the same time urging said narrow end to remain axially aligned with said wide end after folding over said conduit;

10. The conduit holder according to claim 9, wherein said wide and narrow ends of said strap means are looped around said conduit in opposite directions by passing from under said conduit, up around said conduit, and back down to said base plate means on opposite sides of said conduit.

11. The conduit holder according to claim 9, wherein said base plate means further comprises a sheet for covering said adhesive coating which is easily removed when it is desired to attach said base plate means to the skin of the patient.

12. The conduit holder according to claim 9, wherein said base plate means may be easily trimmed to fit awkward areas of the patient without compromising its effectiveness in providing secure attachment means for said medical conduit.

13. A method of securing medical conduit to the skin surface of a patient comprising the steps of:

removing a protective sheet from a lower adhesive side of a base plate having an upper attachment surface;

adhering said base plate to the skin surface near the approximate location where it is desired to secure said conduit;

orienting said conduit orthogonally to strap means having a wide end with a cutout, a narrow end, and central zone where said wide and narrow ends merge, said central zone being fixed to said base plate;

positioning said conduit above said central zone of said strap means where said wide and narrow ends merge;

folding said narrow end of said strap means up and over said conduit without twisting in one direction;

folding said wide end of said strap means up and over said conduit without twisting and opposite said one direction;

passing said narrow end through said cutout;

tensioning said strap means by pulling said wide and narrow ends apart so as to firmly cinch said conduit within said loop;

lowering said strap ends, while maintaining said tension, to close proximity with said base plate; and simultaneously pressing said wide and said narrow ends of said strap means down against said upper attachment surface of said base plate so as to anchor said strap means, said folds and said encircled conduit in place with respect to said patient.

* * * * *